US006455269B1

(12) United States Patent
Toombs (10) Patent No.: US 6,455,269 B1
(45) Date of Patent: Sep. 24, 2002

(54) METHOD FOR LOCALIZED ADMINISTRATION OF FIBRINOLYTIC METALLOPROTEINASES

(75) Inventor: Christopher F. Toombs, Camarillo, CA (US)

(73) Assignee: Amgen, Inc., Thousand Oaks, CA (US)

(*) Notice: Subject to any disclaimer, the term of this patent is extended or adjusted under 35 U.S.C. 154(b) by 0 days.

(21) Appl. No.: 09/466,276

(22) Filed: Dec. 17, 1999

(51) Int. Cl.$^7$ ................................. C12Q 1/37

(52) U.S. Cl. .................................. 435/23; 435/13

(58) Field of Search .................. 435/23, 13, 69.2, 435/212, 217; 424/94.64, 94.67, 145.1; 514/822; 530/324

(56) References Cited

U.S. PATENT DOCUMENTS

| | | | |
|---|---|---|---|
| 4,447,236 A | 5/1984 | Quinn | |
| 5,626,564 A | 5/1997 | Zhan et al. | |
| 5,709,676 A | 1/1998 | Alt | |
| 5,830,468 A | 11/1998 | Bini | 424/94.67 |
| 5,865,178 A | 2/1999 | Yock | |
| 5,922,322 A | 7/1999 | Bini | 424/94.67 |
| 5,951,981 A * | 9/1999 | Markland, Jr. et al. | 424/94.67 |
| 6,020,181 A * | 2/2000 | Bini | 435/226 |
| 6,107,280 A * | 8/2000 | White et al. | 514/12 |

FOREIGN PATENT DOCUMENTS

| | | |
|---|---|---|
| EP | 0 323 722 | 7/1989 |
| WO | WO 90/07352 | 7/1990 |
| WO | WO 01/24817 | 4/2001 |
| WO | WO 01/25445 A1 | 4/2001 |

OTHER PUBLICATIONS

Ahmed N. K. Biological and Thrombolytic Properties of Fibrolase. Haemostasis 20:334–340, 1990.*
Markland F. Thrombolytic Effecfs of Recombinant Fibrolase or APSAC in a Canine Model of Carotid Artery Thrombosis. Circulation 9(5)2448–56, 1994.*
Kandarpa et al., Foreceful Pulsatile Local Infusion of Enzyme Accelerates Thrombolysis: In Vivo Evaluation of a New Delivery System, *Radiology*, (1981) 168: 739–744.
Guan et al., Archives of Biochemistry and Biophysics, vol. 289, No. 2, pp. 197–207 (1991).
Randolph et al., Protein Science, Cambridge University Press, pp. 590–600 (1992).
Ahmed et al., Haemostasis, vol. 20, pp. 147–154 (1990).
Markland et al., Circulation, vol. 9, No. 5, pp. 2448–2456 (1994).
Manning, Toxicon, vol. 33, No. 9, pp. 1189–1200 (1995).
Retzios et al., Thrombosis Research, vol. 74, No. 4, pp. 355–367 (1994).
Pretzer et al., Pharmaceutical Research, vol. 8, No. 9, pp. 1103–1112 (1991).
Pretzer et al., Pharmaceutical Research vol. 9, No. 7, pp. 870–877 (1992).
Methods in Enzymology, edited by A.J. Barrett, Academic Press, Inc., Philadelphia, PA, pp. 737–754 (1981).

* cited by examiner

*Primary Examiner*—Ralph Gitomer
(74) *Attorney, Agent, or Firm*—Karen L. Nicastro; Ron K. Levy; Steven M. Odre (57) ABSTRACT

A method is provided for the localized intravascular administration of a fibrinolytic metalloproteinase to a human subject in amounts that are both safe and effective to lyse an occluding fibrin-containing blood clot, while also avoiding the neutralizing effects of $\alpha_2$-macroglobulin in the circulating blood.

14 Claims, 4 Drawing Sheets

Histogram of Estimated Maximum Dose of NAT in
Patients with Peripheral Vascular Occlusion

METHOD FOR LOCALIZED ADMINISTRATION OF FIBRINOLYTIC METALLOPROTEINASES

FIELD OF THE INVENTION

This invention relates to the therapeutic administration of fibrinolytic metalloproteinases, and more specifically to a method for administering such agents in vivo via localized delivery to vascular thrombi in order to effect clot lysis.

BACKGROUND OF THE INVENTION

Vascular occlusions caused by blood clots such as thrombi and embolisms are serious medical maladies that can become limb or life threatening if not timely treated. Devices and methods have been developed for the treatment and removal of vascular blood clots. By way of illustration, see U.S. Pat. No. 4,447,236 (Quinn), issued May 8, 1984; U.S. Pat. No. 4,692,139 (Stiles), issued Sep. 8, 1987; U.S. Pat. No. 4,755,167 (Thistle et al.), issued Jul. 5, 1988; U.S. Pat. No. 5,167,628 (Boyles), issued Dec. 1, 1992; U.S. Pat. No. 5,222,941 (Don Michael). issued Jun. 29, 1993; U.S. Pat. No. 5,250,034 (Appling et al.), issued Oct. 5, 1993: U.S. Pat. No. 5,370,653 (Cragg), issued Dec. 6, 1994; U.S. Pat. No. 5,380,273 (Dubrul et al.), issued Jan. 10, 1995; U.S. Pat. No. 5,498,236 (Dubrul et al.), issued Mar. 12, 1996; U.S. Pat. No. 5,626,564 (Zhan et al.), issued May 6, 1997; U.S. Pat. No. 5,709,676 (Alt), issued Jan. 20, 1998; U.S. Pat. No. 5,865,178 (Yock), issued Feb. 2, 1999, and WO 90/07352 (published Jul. 12, 1990). Such methods and devices include infusion catheters for delivering thrombolytic or fibrinolytic agents to the blood clot and dissolving it. Infusion catheters are typically used in conjunction with enzymatically active agents that are capable of degrading the fibrin in the clot and thus effectively dissolving the clot. Such enzymes are typically referred to as "thrombolytic" or "fibrinolytic" agents.

Fibrolase is a known fibrinolytic zinc metalloproteinase that was first isolated from the venom of the southern copperhead snake (*Agkistrodon contortrix contortrix*). See Guan et al., Archives of Biochemistry and Biophysics, Volume 289, Number 2, pages 197–207 (1991); Randolph et al., Protein Science, Cambridge University Press (1992), pages 590–600; European Patent Application No. 0 323 722 (Valenzuela et al.), published Jul. 12, 1989; and U.S. Pat. No. 4,610,879 (Markland et al.), issued Sep. 9, 1986. Fibrolase has been shown to be fibrinolytic, and this metalloproteinase has been documented to have proteolytic activity against the fibrinogen Aα-chain, with reduced proteolytic cleavage of the Bβ-chain and no activity against the γ-chain of fibrinogen; Ahmed et al., Haemostasis, Volume 20, pages 147–154 (1990). Because fibrin is a principal component of blood clots, the fibrinolytic properties of fibrolase point to its potential as a clot dissolving agent for in vivo thrombolytic use; see Markland et al., Circulation, Volume 9, Number 5, pages 2448–2456 (1994), and Ahmed et al., above.

Novel Acting Thrombolytic (NAT) is a modified form of fibrolase that differs from fibrolase in that NAT contains 201 amino acids with an N-terminal sequence of SFPQR, whereas the N-terminal sequence of native fibrolase begins with EQRFPQR and is 203 amino acids in length. The amino-terminal modification was designed to prevent chemical reactions at amino acid residues that were capable of forming a variable quantity of cyclized glutamine (pyroglutamic acid) which have the potential to create lot-to-lot variations in quality and uniformity of the product. Thus, NAT can be viewed as a more stable molecule.

Despite these structural differences, NAT and fibrolase are similar with respect to enzymatic (fibrinolytic) activity. This similarity in biological activity is consistent with data indicating that the active site of the fibrolase molecule spans amino acids 139–159, as described by Manning in Toxicon, Volume 33, pages 1189–1200 (1995), and its predicted location in three-dimensional space is distant from the amino-terminus. The active site of the fibrolase and NAT molecules contains a zinc atom which is complexed by three histidine residues.

Published literature on venom-derived fibrolase has demonstrated its proteolytic activity against fibrinogen at the $Lys^{413}$-$Leu^{414}$ site and against the oxidized β-chain of insulin at the $Ala^{14}$-$Leu^{15}$ site; Retzios and Markland, Thrombosis Research, Volume 74, pages 355–367 (1994); Pretzer et al., Pharmaceutical Research, Volume 8, pages 1103–1112 (1991), and Pretzer et al., Pharmaceutical Research, Volume 9, pages 870–877 (1992). NAT has also been determined to have proteolytic activity on these substrates at the same cleavage sites.

In contrast to fibrinolytic metallo-proteinases such as fibrolase and NAT, clot lysing agents such as streptokinase, urokinase and tissue-type plasminogen activator (tPA) are plasminogen activators which promote thrombolysis by activation of the endogenous fibrinolytic system. More specifically, plasminogen activators catalyze the conversion of plasminogen into plasmin, a serine protease. Plasmin is capable of cleaving fibrinogen and fibrin at arginyl-lysyl bonds, and it is through the generation of plasmin that the plasminogen activators ultimately effect fibrin degradation and clot lysis. Current commercially available thrombolytic agents are plasminogen activators, such as urokinase, streptokinase or tPA.

Unlike the plasminogen activator class of thrombolytic drugs, fibrinolytic metalloproteinases, such as fibrolase and NAT, do not rely on the endogenous fibrinolytic system (conversion of plasminogen to plasmin). Hence, this class of clot lysing agents can be distinguished from the plasminogen activators by their unique mode of action and are defined as "direct" fibrinolytic agents.

Alpha$_2$-macroglobulin is a prevalent proteinase inhibitor present in mammalian serum and is one of the largest of the serum proteins (having a molecular weight of 725 kilodaltons). The specificity of $α_2$-macroglobulin for proteinases is broad, encompassing serine, cysteine, aspartic and metalloproteinase classes. The $α_2$-macroglobulin molecule is a tetramer of identical subunits that are disulfide bonded in pairs with a non-covalent association of the half molecules. Thus, under reducing conditions, native $α_2$-macroglobulin can be dissociated into its four monomeric subunits.

Each subunit of $α_2$-macroglobulin possesses a region that is very susceptible to proteolytic cleavage (the "bait" region). Proteolysis of the bait region induces a conformational change in $α_2$-macroglobulin, which entraps the proteinase within the $α_2$-macroglobulin molecular structure. This process is described in the literature as a "venus fly-trap" interaction. Once the proteinase is entrapped, it is sterically hindered and therefore cannot access its macromolecular substrate.

In addition, a covalent bond can form between $α_2$-macroglobulin and many of the proteinases that it entraps. As mentioned, entrapment of a proteinase induces a conformational change in the $α_2$-macroglobulin molecule. It is presumed that upon this conformational change, a thioester bond on the interior of the $α_2$-macroglobulin molecule becomes reactive and can form a covalent bond with nucleophilic residues (such as lysine) of the entrapped proteinase. Thus, within the general circulation, $\alpha_2$-macroglobulin can effectively neutralize a variety of proteinases.

Moreover, the conformational change in $\alpha_2$-macroglobulin brought about by the entrapment of a proteinase results in a form that is recognized by the reticuloendothelial system. Clearance of $\alpha_2$-macroglobulin-entrapped proteinases is generally described with half-life values in minutes and is believed to occur through the low-density lipoprotein (LDL)-receptor related protein expressed on macrophages, hepatocytes and fibroblasts. For more on $\alpha_2$-macroglobulin, see Methods in Enzymology, edited by A. J. Barrett, Academic Press, Inc., Philadelphia, (1981), pages 737–754.

Alpha$_2$-macroglobulin is capable of forming a macromolecular complex with fibrolase, NAT and other proteinases. Unlike some proteinases that can form a dissociable complex with $\alpha_2$-macroglobulin, fibrolase and NAT are two examples of fibrinolytic metalloproteinases that form a complex which cannot be dissociated from $\alpha_2$-macroglobulin under physiologic conditions. When purified human $\alpha_2$-macroglobulin and NAT, for instance, are incubated together, formation of the complex begins in seconds and is nearly complete within a few minutes. This phenomenon shows that in vitro complex formation can be rapid and is suggestive of the potential rapidity of complex formation between $\alpha_2$-macroglobulin and NAT or other fibrinolytic metalloproteinases in vivo.

Although $\alpha_2$-macroglobulin is one of the major plasma proteins, there is nonetheless a finite quantity of $\alpha_2$-macroglobulin in the circulation that would be available to bind and neutralize a fibrinolytic metalloproteinase. The $\alpha_2$-macroglobulin binding capacity is therefore saturable. Once the $\alpha_2$-macroglobulin binding capacity has been exceeded, the concentration of unbound fibrinolytic metalloproteinase rises proportionally as additional fibrinolytic metalloproteinase is added to the sample.

The presence of $\alpha_2$-macroglobulin in the general circulation of a patient presents a challenge for the systemic (for example, intravenous) administration of fibrolase, NAT and other fibrinolytic metalloproteinases that are bound up by $\alpha$2-macroglobulin in the general blood circulation. Unless the saturable level of innate ($\alpha_2$-macroglobulin is exceeded by the systemically administered dose of such fibrinolytic metalloproteinases, the latter will effectively be neutralized and rendered ineffective for therapeutic purposes.

In one in vivo study, conducted in rabbits, the biological effectiveness of venom-derived fibrolase was examined following systemic intravenous administration. Ahmed et al., Haemostasis, above. The dose of fibrolase used was 3.7 milligrams per kilogram, which was estimated to yield a final blood concentration of approximately 60 micrograms per milliliter in a 3.0-kilogram rabbit. This amount was chosen based on studies examining the inactivation of the enzyme in the presence of blood or plasma, presumably due to $\alpha_2$-macroglobulin (see pages 336 and 339).

In another in vivo study, the biological effect of recombinant fibrolase on clot lysis was examined in canines. Markland et al., Circulation, above. Four milligrams of this material per kilogram (of animal body weight) was infused over five minutes proximal to a pre-induced thrombus in the left carotid artery via a catheter device (see page 2450). Here again, it was noted that inactivation of fibrolase occurs in the general blood circulation presumably due to the presence of $\alpha_2$-macroglobulin (see page 2454, second column, last paragraph).

As these two studies show, the deactivating effects of $\alpha_2$-macroglobulin can be overcome by either administration or systemic dosages of fibrinolytic metalloproteinase that exceed the saturable level of innate $\alpha_2$-macroglobulin (the rabbit study) or by delivering the enzyme locally to the site of the clot (the dog study) and avoiding systemic administration. On the other hand, doses of the fibrinolytic metalloproteinase in excess of the saturable level of $\alpha_2$-macroglobulin, whether delivered systemically or locally, may exceed levels that are safe and well tolerated by the subject being treated. Notably, fibrinolytic metalloproteinases are capable of destroying not only fibrin, but they may also degrade other structural proteins and are therefore potentially toxic in vivo when present in large amounts that exceed the saturable level of $\alpha_2$-macroglobulin.

It is an object of the present invention to provide a safe and biologically effective way of using locally administered fibrinolytic metalloproteinases to lyse blood clots in vivo.

SUMMARY OF THE INVENTION

Briefly stated, this invention is a method for the treatment of a blood clot in vivo, in human subjects, by a fibrinolytic metalloproteinase, comprising locally administering a safe, biologically effective amount of the fibrinolytic metalloproteinase to the blood clot, such as by use of catheter delivery means.

By "safe, biologically effective" amount is meant an amount sufficient to degrade fibrin and facilitate lysing of the clot (i.e., thrombus), while not exceeding levels significantly above the saturable level of ($\alpha_2$-macroglobulin in the circulatory system of the patient being treated (i.e., levels that may cause damage to blood vessel walls). Typically, this amount will be in the range between 0.025 and 1.7 milligrams per kilogram of body weight for the human subject being treated, as determined from a study conducted with blood samples from human subjects that have been studied for in vitro $\alpha_2$-macroglobulin content and binding capacity. From the in vitro results of this study, it has been possible to define the saturable level in vivo of $\alpha_2$-macroglobulin for all practical purposes, thus enabling the delineation of a biologically effective amount that takes into account not only the minimum level of fibrinolytic metalloproteinase required for biological effectiveness, but also the maximum level for well tolerated administration. This study is described in detail further below among the Examples.

The method of this invention is applicable for in vivo therapeutic use in the treatment of stationary fibrin clots located in either native arterial or venous blood vessels, or in synthetic arterial or venous grafts, in humans.

The terms "locally" or "localized" as applied to the form of delivery of the fibrinolytic metalloproteinase herein refer to intra-arterial or intravenous administration either directly to the blood clot itself (i.e., intrathrombus) or in close proximity to the clot (either proximal or distal relative to blood flow) and near enough for the majority of the fibrinolytic metalloproteinase to be absorbed by the clot.

The term "catheter delivery means" is employed herein in the conventional sense of referring to a tubular medical device for insertion into canals, vessels, passageways or body cavities for the purpose of injecting or withdrawing fluids or to keep a passageway open. In general, such means will typically comprise an elongated flexible catheter body containing one or more interior passageways (or "lumens"); a proximal portion which allows material (i.e., clot lysing agent) to be introduced into the catheter body and to flow through the lumen; a distal portion optionally having a tapered end; and multiple exit ports at or near the end of the distal portion to permit material to exit the catheter in response to applied pressure.

The method of this invention is illustrated further below with respect to peripheral artery occlusion (PAO). PAO finds its origins in peripheral vascular disease due to atherosclerosis. The symptoms develop slowly over many years as atherosclerosis progresses, with a critical ischemic level being reached in about 15 to 20% of patients with lower extremity disease. Medical therapy is limited and predominantly aimed at prevention or risk reduction using medications such as lipid-lowering or antiplatelet agents, smoke cessation programs and physical exercise. Jackson and Clagett, Chest, Volume 114, pages 666S–682S (1998).

The clinical manifestations of peripheral vascular disease may include acute occurrences of limb-threatening ischemia or the presence of more chronic evidence of vascular disease (i.e., intermittent claudications). Outside of the aforementioned preventive measures, chronic PAO is typically not treated until the onset of severe lifestyle limitation or limb-threatening ischemia. Depending on the vessel segment affected and the extent of occlusion, available medical interventions include percutaneous transluminal angioplasty, surgical revascularization, and thrombolysis. Studies have shown that the intra-arterial infusion of clot lysing agents, particularly in the early stages of occlusion, can avoid the need for surgical intervention. As demonstrated in the Rochester trial, which compared thrombolysis with the plaminogen activator urokinase to surgery in the treatment of acute PAO (Ouriel et al., Journal of Vascular Surgery, 1994, Volume 19, pages 1021–1030), approximately 33 percent of patients in the thrombolysis arm of the study were successfully treated with medical intervention only, thereby avoiding a more invasive procedure. In contrast, 98 percent of patients in the operating arm were subjected to an endovascular or surgical procedure.

Other medical disorders involving occlusive blood clots can be effectively treated in a similar manner by the present method, including, but not limited to, acute myocardial infarction, ischemic stroke, deep venous thrombosis and pulmonary embolism. The method of this invention can also be employed to dissolve clots which occur with chronically implanted medical devices such as indwelling catheters and hemodialysis access grafts.

BRIEF DESCRIPTION OF THE FIGURES

FIGS. 1A–1C.

DETAILED DESCRIPTION OF THE INVENTION

The method of this invention is applicable for the therapeutic delivery of any fibrinolytic metalloproteinase that is capable of being complexed with $\alpha_2$-macroglobulin. Such fibrinolytic metalloproteinases, if naturally occurring, may be purified from their natural sources, e.g., fibrolase from snake venom. Alternatively, polypeptide fibrinolytic metalloproteinase agents the nucleic acid and amino acid sequences of which are known may be produced by utilizing conventional methods of recombinant expression and purification.

In general, recombinant methods employ a DNA molecule encoding the fibrinolytic metalloproteinase of interest which is inserted into an appropriate vector for expression in a suitable host cell. The vector is selected to be functional in the particular host cell employed, i.e., is compatible with the host cell machinery, such that expression of the DNA can occur. The vectors may also contain a 5' flanking sequence (also referred to as a "promoter") and other expression regulatory elements operatively linked to the DNA to be expressed, as well as other known elements, such as an origin of replication element, a transcriptional termination element, a complete intron sequence containing a donor and acceptor splice site, a signal peptide sequence, a ribosome binding site element, a polyadenylation sequence, a polylinker region for inserting the encoding nucleic acid, and a selectable marker element. The vector may also optionally contain a "tag" sequence, i.e., an oligonucleotide sequence located at the 5' or 3' end of the polypeptide-coding sequence that encodes polyHis or another small immunogenic sequence. This tag will be expressed along with protein of interest, and can serve as an affinity tag for purification of this polypeptide from the host cell. If desired, the tag can subsequently be removed from the purified polypeptide by various means, for example, with use of a selective peptidase.

In those cases where it is desirable for the polypeptide to be secreted from the host cell, a signal sequence may be used to direct the polypeptide out of the host cell where it is synthesized. Typically, the signal sequence is positioned in the coding region of nucleic acid sequence, or directly at the 5' end of the coding region. Many signal sequences have been identified, and any which are functional in the selected host cell may be used.

After the vector has been constructed and a nucleic acid has been inserted into the proper site of the vector, the completed vector may be inserted into a suitable host cell for amplification and/or polypeptide expression. Host cells may be prokaryotic (such as E. coli) or eukaryotic (such as a yeast cell, an insect cell, or a vertebrate cell).

Suitable host cells or cell lines may be mammalian cells, such as Chinese hamster ovary cells (CHO) or 3T3 cells. The selection of suitable mammalian host cells and methods for transformation, culture, amplification, screening and product production and purification are known in the art. Other suitable mammalian cell lines are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Still other suitable mammalian cell lines include but are not limited to, HeLa, mouse L-929 cells, 3T3 lines derived from Swiss, Balb-c or NIH mice, BHK or HaK hamster cell lines.

Also useful as host cells are bacterial cells, for example, various strains of E. coil, and various strains of yeast cells.

Insertion (also referred to as "transformation" or "transfection") of the vector into the selected host cell may be accomplished using such methods as calcium phosphate, electroporation, microinjection, lipofection or the DEAE-dextran method. The method selected will in part be a function of the type of host cell to be used. These methods and other suitable methods are well known to the skilled artisan.

The host cell, when cultured under appropriate conditions, can synthesize the fibrinolytic metalloproteinase of interest. The host cells may be cultured using standard media well known to the skilled artisan. The media will usually contain all nutrients necessary for the growth and survival of the cells. Suitable media for culturing *E. coli cells* are, for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of protein produced in the host cell can be evaluated using standard methods known in the art, including Western blot analysis, SDS-polyacrylamide gel electrophoresis, non-denaturing gel electrophoresis, HPLC separation, immunoprecipitation, and/or activity assays such as DNA binding gel shift assays.

If the protein is secreted from the host cells other than gram-negative bacteria, the majority will likely be found in the cell culture medium. If it is not secreted, it will be present in the cytoplasm. For intracellular protein, the host cells are typically first disrupted mechanically. For protein having a periplasmic location, either mechanical disruption or osmotic treatment can be used to release the periplasmic contents into a buffered solution, and the polypeptide is then isolated from this solution. Purification from solution can thereafter be accomplished using a variety of techniques.

If the protein has been synthesized so that it contains a tag such as hexahistidine or other small peptide at either its carboxyl or amino terminus, it may essentially be purified in a one-step process by passing the solution through an affinity column where the column matrix has a high affinity for the tag or for the polypeptide directly (i.e., a monoclonal antibody). Where the polypeptide has no tag and no antibodies are available, other well known procedures for purification can be used, for example, ion exchange chromatography, molecular sieve chromatography, reversed phase chromatography, HPLC, native gel electrophoresis in combination with gel elution, and preparative isoelectric focusing ("Isoprime" machine/technique, Hoefer Scientific). In some cases, two or more of these techniques may be combined to achieve increased purity.

Novel Acting Thrombolytic (NAT) polypeptide utilized herein to illustrate the practice of this invention refers in general to the fibrinolytically active metalloproteinase of SEQ ID NO: 1. The NAT polypeptide is encoded by the cDNA molecule of SEQ ID NO: 2, although any DNA molecule of variant sequence encoding the same polypeptide may be used for expression and manufacture in accordance with specific methods which are referred to further below.

Fibrolase has been described in the scientific and patent literature; see references above. Typically, the form of fibrolase which is employed in the practice of this invention will be of SEQ ID NO: 3, which is encoded by the cDNA molecule of SEQ ID NO: 4 or variants thereof encoding the same amino acid sequence.

Preferably, a yeast expression system is employed for recombinant expression of NAT. Special mention is made of Pichia strains, for example, *Pichia pastoris,* as being the most advantageous and preferred for use. A detailed description of such a system may be found in U.S. Pat. No. 4,855,231 (Stroman et al.), U.S. Pat. No. 4,812,405 (Lair et al.), U.S. Pat. No. 4,818,700 (Cregg et al.), U.S. Pat. No. 4,885,242 (Cregg), and U.S. Pat. No. 4,837,148 (Cregg), the disclosures of which are hereby incorporated by reference. Expression of fibrolase in such a system will typically involve a DNA molecule of SEQ ID NO: 5, which encodes "prepro" sequence (nucleotides 1–783) in addition to the "mature" polypeptide (nucleotides 784–1392). The expression of NAT in such a system will typically involve a DNA molecule of SEQ ID NO: 6, which encodes "prepro" sequence (nucleotides 1–783) in addition to the "mature" polypeptide (nucleotides 784–1386).

The fibrinolytic metalloproteinase employed in accordance with this invention, whether it be NAT, fibrolase, or some other fibrinolytic metallo-proteinase, is administered in the form of a pharmaceutically acceptable solution, alone or containing additional pharmaceutically acceptable ingredients. If desired, such solutions may comprise, in addition to the fibrinolytic metalloproteinase and a solvent (i.e., distilled water or physiological saline), standard ingredients such as stabilizers (to prevent protein aggregation or physical or chemical degradation in aqueous media), bulking agents (to provide bulk), diluents, antibacterial agents, viscosity adjusting agents, anti-oxidants, and so forth, in conventional amounts. Known excipients which can be included in the formulation include polyols (including mannitol, sorbitol and glycerol); sugars (including glucose and sucrose); and amino acids (including alanine, glycine and glutamic acid). See, for example, Remington's Pharmaceutical Sciences, Mack Publishing Company, Easton, Pa.

Desirably, the pharmaceutical composition will be buffered (with a biocompatible buffering agent, for example, citric acid or citric acid salt) to a pH which is at or near neutral (7.0) prior to administration, and usually between about 6.5 and about 8.0 pH (±0.5).

If the metal ion of the fibrinolytic metalloproteinase is zinc, such as with fibrolase or NAT, it may be preferable to include a water soluble zinc salt (for example, zinc sulfate or zinc acetate) as a stabilizer. To further enhance the long-term stability and shelf life of the composition, it may also be advantageous to freeze the solution or to convert it to a lyophilized (freeze-dried) product which is thawed or reconstituted prior to use, as the case may be.

By way of illustration, a freezable liquid medicinal composition which may be employed in the method of this invention comprises fibrolase or NAT, a water soluble zinc salt, a citric acid buffer, optionally an additional stabilizer selected from the group consisting of water soluble calcium salts, and optionally a bulking agent (for example, mannitol). A surfactant, such as Tween 80 (BASF, Gurnee, Ill.), may also be added to increase freeze-thaw stability. Tris buffer (Sigma, St. Louis, Mo.) or another buffer with a buffer capacity above pH 7.0 may be added to stabilize the pH at or above pH 7.4. Most of these ingredients will be present in minor amounts ranging from 0.001 to 2.0 millimolar (mM) or less than ten percent (W/V). The buffering agent will be added in an amount sufficient to achieve the desired pH, and this amount may vary depending on the specific formulation.

By way of further illustration, a lyophilizable or lyophilized pharmaceutical composition which can be used in the method of this invention comprises fibrolase or NAT, a zinc stabilizer (e.g., water soluble zinc salt such as the above), and a citric acid buffer, with or without other excipients (e.g., bulking agent such as mannitol, glycine, or the like). The lyophilized composition may also contain a disaccharide sugar, such as sucrose or trehalose, as a lyoprotectant. A surfactant, such as Tween 80, may be added to protect against lyophilization stresses on the fibrinolytic metalloproteinase (e.g., fibrolase or NAT). The pH will ideally be maintained at pH 8.0±0.5, using a suitable buffer with a $PK_a$ in this range (for example, Tris). Amounts of ingredients will be in accordance with the above.

As mentioned, the method of this invention is employed to locally administer biologically effective amounts of a fibrinolytic metalloproteinase that are in the range between 0.025 and 1.7 mg/kg. Preferably, this amount will in the range from about 0.1 to about 0.5 mg/kg. Solution strengths will be formulated accordingly, with dilution be effected as needed upon administration.

In the typical case, the method of this invention is carried out in conjunction with a catheter-directed thrombolysis procedure. Such procedures involve the use of a pre-sterilized catheter-type drug delivery device, the side walls of which may be made of a thin, semi-rigid or flexible biocompatible material (for example, a polyolefin, fluoropolymer, or other inert polymer). In general, suitable catheters contain at least one interior cavity (or lumen) running the length of the device. The material from which the catheter is constructed is flexible enough to be moved through the interior of the vasculature without causing injury to the blood vessel walls, yet sufficiently rigid to extend over a distance to the site of treatment while the interior cavity of the device remains fully distended. Typically, such catheter devices will range from 2 to 20 on the French scale for catheter diameters (⅓ millimeter equals 1 French) and from two to six feet or more in length.

Figure 2:
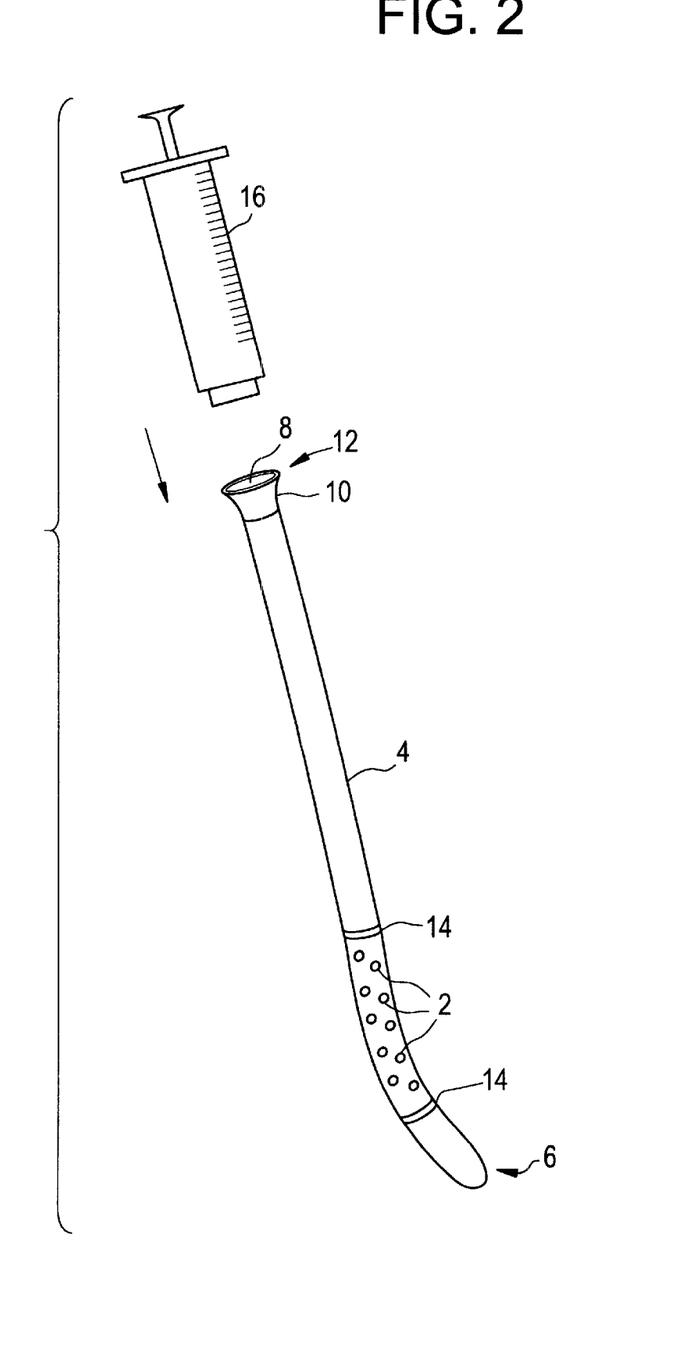
FIG. 2 illustrates a type of catheter device designed for localized delivery of a thrombolytic agent in a blood vessel.
Figure 3:
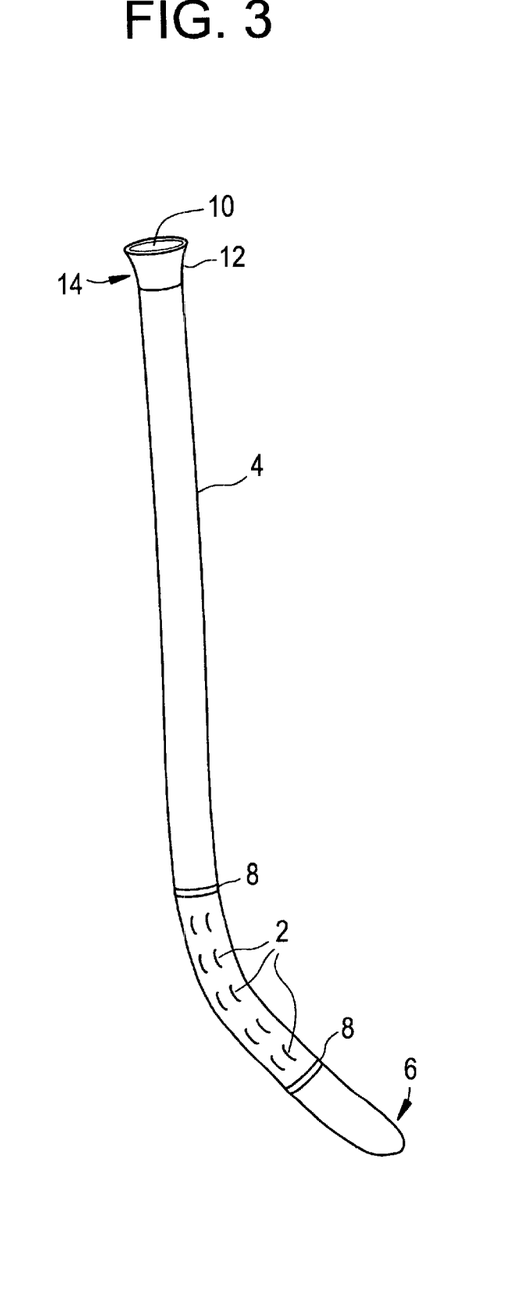
FIG. 3 is a side cross-sectional view of an alternate type of catheter device for localized delivery of a thrombolytic agent in a blood vessel.

Exemplary catheter devices for the intravascular delivery of thrombolytic medication in accordance with this invention are illustrated in FIGS. 2 and 3, the practical applications of which are described in detail in the examples below. However, any conventional catheter delivery device which is suitable for this method may be utilized, including but not limited to the specific devices referred to herein.

An effective dose of fibrinolytic metalloproteinase can be delivered through the catheter to the local site of treatment by pulsatile infusion, continuous infusion, bolus administration, or a combination of all three. The solution strength (i.e., concentration) of fibrinolytic metalloproteinase in the treatment solution is an important parameter. More specifically, a range between the minimum dilution of the fibrinolytic metalloproteinase for effectiveness at the lower end (which is especially important for bolus administration) and the maximum solubility of the fibrinolytic metalloproteinase at the higher end should be selected. In general, solution strengths in the range from about 0.1 to about 80 mg/mL are employed. The volume of the bolus (or total volume of multiple boluses in the case of a "pulsed" delivery) is then selected accordingly to deliver an effective amount of fibrinolytic metalloproteinase within the ranges prescribed above.

DESCRIPTION OF THE FIGURES

Figure 1A:
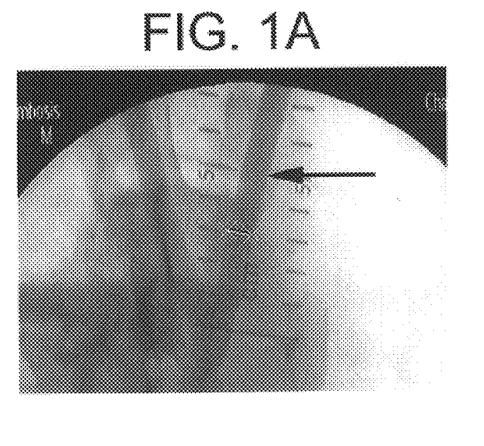
FIG. 1A is a baseline angiogram of the carotid artery in an adult pig prior to balloon catheter induced-injury and the formation of an occlusive thrombus.
Figure 1B:
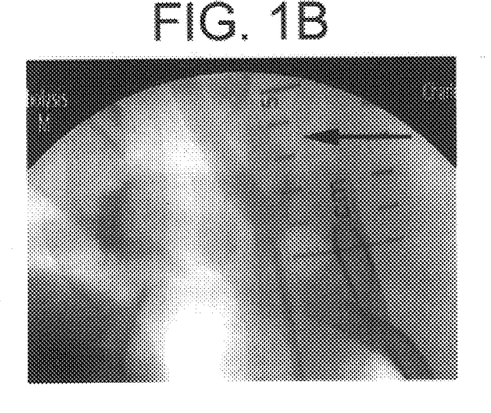
FIG. 1B is an angiogram taken four days following formation of said thrombus in the same animal and prior to the administration of NAT in accordance with the method of this invention.
Figure 1C:
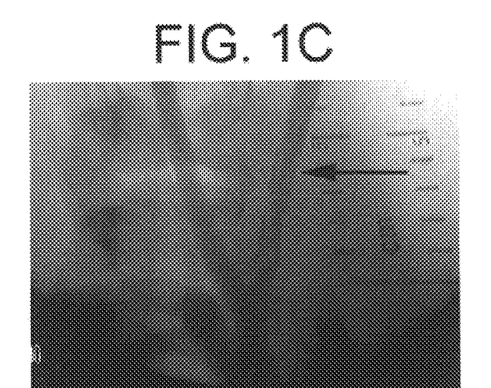
FIG. 1C is an angiogram at 2 hours following administration of 30 mg of NAT through a "PRO" catheter (see FIG. 3 for an illustration of this device).

FIGS. 1A–1C. FIG. 1A is a baseline angiogram of the carotid artery in an adult pig prior to balloon catheter induced-injury and the formation of an occlusive thrombus. The arrow indicates the position and the presence of contrast media in the left common carotid artery, indicating that blood flow in the artery which is unobstructed (i.e., the blood vessel is "patent" or has "patency"). FIG. 1B is an angiogram taken four days after formation of said thrombus in the same animal and prior to the administration of NAT in accordance with the method of this invention. The arrow indicates the position of the left common carotid artery, however, contrast media does not flow in the artery due to the presence of an occlusive thrombus. FIG. 1C is an angiogram at 2 hours following administration of 30 mg of NAT through a "PRO" catheter (see FIG. 3 for an illustration of this device). The arrow indicates the presence of contrast media in the vessel, demonstrating that patency has been restored in the left carotid artery. Minimal residual thrombus is visible in the lumen of the artery.

FIG. 2 illustrates a type of catheter device designed for localized delivery of a thrombolytic agent in a blood vessel. The device, shown here in side cross-sectional view, contains "side holes" at the delivery end through which the infusate (thrombolytic agent) is emitted under applied fluid pressure. The diameters of the catheter tubes in this figure and the following figure relative to overall size are exaggerated to show the details better.

FIG. 3 is a side cross-sectional view of an alternate type of catheter device for localized delivery of a thrombolytic agent in a blood vessel. This device contains thin slits, referred to as "pressure response outlets" (PRO), which have been cut into the catheter wall at regular intervals such that infusate escapes when the fluid pressure within the catheter reaches a critical point, causing the slit to open. The device can be used in conjunction with an automated, piston-driven, pulsed infusion device (not shown, but exemplified further below) which is capable of delivering pulses of drug infusion.

DESCRIPTION OF SPECIFIC EMBODIMENTS

The invention is further illustrated in the following examples, which are meant to be illustrative only and not to limit the invention to the described embodiments. In these examples, and throughout the description of this invention, "kg" indicates kilograms of body weight per test subject, "mg" indicates milligrams, "mL" indicates milliliters, and "min" indicates minutes. The fibrinolytic metalloproteinase illustrated, namely Novel Acting Thrombolytic (NAT), was recombinant-derived and made in accordance with methods referred to above.

EXAMPLE 1

Thrombolysis in Subacute Thrombosis of the Adult Pig Common Carotid Artery

NAT was been studied in a model of subacute thrombosis of the carotid artery in adult pigs, averaging 75 kg in body weight, at a contract laboratory (Charles River Laboratories, Southbridge, Mass.). The intent of this study was to establish the fibrinolytic activity of NAT in a thrombosis model which is relevant to peripheral artery occlusion in humans.

In this animal model, the carotid artery was thrombosed along its entire length (approximately 20 centimeters from origin at the aorta to the carotid bifurcation) by a combination of balloon injury, thrombin and stasis. The size of the thrombus approaches the size of thrombus encountered clinically in humans with peripheral arterial occlusion. After successful thrombosis, the animal was allowed to recover for a period of four days. A four-day period was selected to allow extensive cross-linking of fibrin, remodeling of thrombus, and infiltration of cells. Notably, both the size and age of the thrombus in this model are reasonable representations of the size and duration of ischemic symptoms reported in the most recently published TOPAS trial of thrombolysis with plasminogen activators in peripheral arterial occlusion in humans. For reference, see Ouriel et al., New England Journal of Medicine, Volume 338, pages 1105–1111 (1998).

Briefly, the common carotid artery can be thrombosed along its entire length by fluoroscopically directed balloon injury. The balloons that are used are oversized and non-compliant. The balloons are inflated at pressures of up to twelve atmospheres, which causes a crushing injury to the intimal layer of the vessel. While the balloon is inflated, it is moved back and forth in order to strip away the vascular endothelium.

The ballooning procedure is very injurious and creates a highly thrombogenic vessel surface and is repeated throughout the entire length of the common carotid artery. After thoroughly injuring the entire artery, the balloon is withdrawn to a proximal position near the aorta and inflated to occlude flow of blood through the vessel. While occluded, fifty Units of bovine thrombin is injected through the distal port of the balloon catheter in order to stimulate coagulation. The balloon remains inflated for a period of thirty minutes, which results in thrombotic occlusion of the vessel. After thirty minutes, the balloon is deflated and an angiogram is performed to confirm that the vessel has become occluded. With these procedures, occlusion of the vessel was achieved in greater than ninety percent of cases.

Once thrombosed, the balloon catheter, guide catheter and access sheath are removed and the animal is allowed to recover over a period of four days. On the fourth day, the animals are re-anesthetized, the occlusion is reconfirmed, and a multiple side hole drug delivery catheter (see FIGS. 2 and 3) is advanced under fluoroscopic guidance and positioned such that the side holes are located within the thrombus. Thrombolysis with NAT was angiographically observed using fixed NAT dosages which ranged from 10 to 30 mg (or approximately 0.1 to 0.4 mg/kg on a weight adjusted basis), as shown in FIGS. 1A–1C.

As the image in FIG. 1B illustrates, NAT is effective in restoring antegrade flow as assessed by angiography. To be more quantitative, flow in the target vessel is qualitatively scored according to a 4-point scale (ranging from 0 to 3) where:

0=no flow
1=flow estimated to be less than 30% of the contralateral (non-thrombosed) carotid
2=flow estimated to be 30–80% of the contralateral carotid
3=flow which is indistinguishable from the contralateral carotid The image shown in FIG. 1B was scored as flow grade equal to 3, a frequent result in thrombosed vessels treated with a fixed 30 mg dosage of NAT (approximately 0.4 mg/kg in a 75 kg pig). Tables 1–3 in the following examples below illustrate the treatment regimen and mean flow scores derived from serial angiograms. In all of the studies, respiration, body temperature, heart rate and arterial blood pressures were continually monitored and remained within physiologic ranges with no changes observed upon administration of NAT.

EXAMPLE 2

Selection of PRO Catheters and Pulse-Spray Delivery

In the clinical management of peripheral arterial occlusion, thrombolytic agents are delivered through catheters which are positioned near or embedded into the thrombus. As shown in FIGS. 2 and 3, there are two types of catheters.

One variety, the "side hole" catheter (FIG. 2), has tiny round side holes (2) cut into the catheter (4) near closed distal end 6, and an entry port 8 (for the solution of fibrinolytic metalloproteinase) in mating ring 10 affixed at proximal end 12. Catheter 4 is constructed of a flexible, elongated, biocompatible polymer tubing material which is hollow and thin-walled and has a uniform diameter of 2 to 20 French, and preferably 3 to 5 French. The catheter contains two radiopaque markers 14 on the exterior surface near distal end 6 which demarcate the portion of the catheter containing side holes 2. In practice, the catheter is inserted into a surgical opening in the occluded artery or vein and, while being observed via fluoroscopy in accordance with standard approved procedures, is moved carefully through the blood vessel such that distal end 6 is positioned into or near the thrombus. Markers 14, which show up clearly on a fluoroscope image, can serve as a guide for positioning that portion of the catheter such that infusate emerging from side holes 2 will contact the thrombus directly. A pharmaceutical solution of the fibrinolytic metalloproteinase is then injected under gentle pressure from syringe-like reservoir 16 into entry port 8 and is impelled toward distal end 6, emerging through holes 2 into the thrombus, causing degradation of the fibrinous material.

When infusions of a fibrinolytic metalloproteinase are performed using this type of catheter, most of the fibrinolytic agent-containing solution tends to escape through the proximal side holes (i.e., those nearest to drug entry port 8), which has a negative impact in the uniformity of drug delivery at the site of treatment. There is also a possibility of backflow of blood into the catheter through side ports 2 under negative pressure.

Another variety of catheter, also composed of a hollow, thin-walled, biocompatible polymer material, shown in FIG. 3, has extremely thin slits 2 that are laser cut into flexible catheter 4 at regular intervals near closed distal end 6. The slits, which are referred to as pressure response outlets ("PRO"), are tight enough that infusate will not escape unless the fluid pressure within the catheter reaches a critical point and causes the slits to distend simultaneously and thus open temporarily. The catheter can also contain exterior radiopaque markers 8 to assist in the positioning of the device at the site of the thrombus.

Ideally, such "PRO" infusion catheters are used in conjunction with an automated, piston-driven, pulsed infusion device (not shown) that is capable of delivering low volume regulated pulses of drug infusion into entry port 10 in mating ring 12 affixed at proximal end 14 of catheter 4. When a pulse is delivered, the pressure within the catheter rises momentarily. In response, the pressure response outlets (slits 2) open momentarily and allow the infusate (e.g., pharmaceutical solution of fibrinolytic metalloproteinase) to escape. The theoretic advantage of pulsed delivery of infusate and a PRO-type catheter is that infusate is delivered uniformly through the slits along the entire length of the catheter, whereas infusate delivered through the "side hole" catheter (FIG. 2) follows a path of least resistance and flows out the proximal side holes in a non-uniform manner as mentioned.

A pig model of four-day old carotid thrombosis was utilized to assess performance of the above mentioned two catheter types, using fixed dosages of 30 mg of NAT (approximately 0.4 mg/kg in a 75 kg pig). The results are summarized in Table 1.

TABLE 1

Comparison of Angiographic Flow Scores Obtained with
NAT Using Side Hole and PRO Infusion Catheters

| DRUG | DOSE | CATH | DELIV TIME (delivery) | ANGIOGRAPHIC FLOW SCORE | | | | |
|---|---|---|---|---|---|---|---|---|
| | | | | 0 | 30 m | 1 hr | 2 hr | 4 hr |
| NAT n = 5 | 30 mg | CM | 60 min (infusion) | 0.0 ± 0.0 | 1.2 ± 0.4 | 1.6 ± 0.5 | 1.8 ± 0.4 | 2.0 ± 0.7 |
| NAT n = 4 | 30 mg | PS | 60 min (0.1 mL pulse) | 0.0 ± 0.0 | 1.5 ± 0.6 | 1.5 ± 0.6 | 2.3 ± 0.5 | 2.5 ± 0.6 |

CM: Cragg-McNamara ™ valved infusion "side hole" type catheter (Micro Therapeutics, Inc., San Clemente, California).
PS: "pulse-spray" delivery as defined by use of pressure response outlet (PRO) catheter (Uni*Fuse Catheter ™, AngioDynamics, Inc., Queensbury, New York) used in conjunction with automated, pulsed infusion device (PULSE*SPRAY INJECTOR Model PSI-1, AngioDynamics, Inc., Queensbury, New York).

As shown in Table 1, angiographic flow scores in the group treated with the pulse-spray modality showed slightly higher initial flow scores at the thirty-minute angiogram which appeared to persist to the four-hour timepoint. Although statistical differences were not obtained, the angiographic results have generally been judged to be superior. Therefore, a PRO-type catheter in conjunction with pulse-spray delivery is the preferred mode of delivery for a fibrinolytic metalloproteinase in accordance with this invention.

EXAMPLE 3

Assessment of Drug Delivery Time

Acute peripheral arterial occlusion is typically treated with plasminogen activators, such as urokinase, delivered as an infusion which is often twenty-four hours in duration, and occasionally as long as forty-eight hours. The lengthy infusion is presumed to maintain a low level of plasmin generation over a prolonged period of time in order to effectively dissolve the occlusive thrombus. As both NAT and fibrolase are fibrinolytic metalloproteinases, such prolonged infusions may not be necessary. To assess whether the delivery rate affects angiographic clot lysis, a fixed 30 mg dose of NAT (roughly 0.4 mg/kg in a 75 kg pig) was delivered using PRO catheters and the pulse spray device. Using 0.1 mL pulse volumes, a 5 mg/mL NAT solution was delivered over six minutes (ten pulses per minute) or over sixty minutes (one pulse per minute). The results are shown in Table 2.

TABLE 2

Comparison of Drug Delivery Times for NAT
Delivered by PRO Catheter and Pulse-Spray Injector

| DRUG | DOSE | CATH | DELIV TIME (pulse volume) | ANGIOGRAPHIC FLOW SCORE | | | | |
|---|---|---|---|---|---|---|---|---|
| | | | | 0 | 30 m | 1 hr | 2 hr | 4 hr |
| NAT n = 3 | 30 mg | PS | 6 min (0.1 mL) | 0.0 ± 0.0 | 2.7 ± 0.6 | 2.7 ± 0.6 | 2.7 ± 0.6 | 2.7 ± 0.6 |
| NAT n = 3 | 30 mg | PS | 60 min (0.1 mL) | 0.0 ± 0.0 | 0.0 ± 0.0 | 1.0 ± 1.0 | 1.3 ± 1.2 | 1.7 ± 0.6 |

As shown in Table 2, the delivery of 30 mg NAT over six minutes resulted in a mean flow score of 2.7 in the three animals at the thirty-minute angiogram, which persisted out to the four-hour timepoint. In contrast, the delivery of 30 mg of NAT by pulsed infusion over sixty minutes was far less impressive. Although these data have not been statistically compared, the results appear to favor delivery of NAT as a more rapid pulse regimen.

EXAMPLE 4

Optimization of Pulse Volume

The pulse-spray infusion device is programmable for delivering pulse volumes of 0.1 to 0.5 mL per pulse. To determine if the pulse volume had any effect on the angiographic outcomes in the pig model, pulse volumes of 0.2 mL were compared to pulse volumes of 0.4 mL. NAT was delivered at a fixed dose of 10 mg (equivalent to 0.15 mg/kg in a 75 kg pig). The results are shown in Table 3.

TABLE 3

Comparison of Angiographic Results Using NAT
Delivered in Pulse Volumes of 0.2 mL or 0.4 mL

| DRUG | DOSE | CATH | DELIV TIME (pulse volume) | ANGIOGRAPHIC FLOW SCORE | | | | |
|---|---|---|---|---|---|---|---|---|
| | | | | 0 | 30 m | 1 hr | 2 hr | 4 hr |
| NAT n = 7 | 10 mg 2.5 mg/mL | PS | 5 min (0.2 mL q15 sec) | 0.0 ± 0.0 | 1.0 ± 0.6 | 1.1 ± 0.7 | 1.6 ± 1.0 | 1.4 ± 1.1 |
| NAT n = 6 | 10 mg 2.5 mg/mL | PS | 5 min (0.4 mL q30 sec) | 0.0 ± 0.0 | 1.2 ± 0.4 | 1.0 ± 0.6 | 0.8 ± 0.8 | 1.0 ± 0.6 |

As shown in Table 3, at thirty minutes the mean angiographic score was slightly higher in the 0.4 mL pulse volume group. However, at the four-hour time point, the group mean was slightly higher in the 0.2 mL pulse volume. As such, no conclusion can be drawn from these studies with regard to one pulse volume being superior to another.

The results in preceding text and tables suggest that virtually all of these NAT treatment regimens are effective in treating peripheral artery occlusions with the method of delivery of this invention, and that these results are at least comparable to treatment with plasminogen activators, such as urokinase, which is the current treatment of choice with thrombolytic agents.

The results demonstrate that the PRO catheter with pulse-spray delivery appears to provide superior angiographic results. Given the body weight of animals in these studies (70–100 kg), the fixed dosage of 30 mg is roughly equivalent to 0.3–0.4 mg/kg on a weight-adjusted basis.

Lowering the fixed dosage NAT to 10 mg resulted in a reduction of group mean angiographic scores at four hours and in some animals, patency was not achieved. This indicates that a dose of 10 mg of NAT appears to be a threshold dose for biologic activity in this model. Given the body weight of animals in these studies (70–100 kg), the fixed dosage of 10 mg is roughly equivalent to 0.1–0.15 mg/kg on a weight-adjusted basis. Varying the pulse volume from 0.2 mL to 0.4 mL did not appear to profoundly impact the angiographic patency scores.

EXAMPLE 5

Establishment of Safe, Well Tolerated, Biologically Effective Dose Range in Humans No satisfactory literature exists on the serum concentration or biochemical activity of $\alpha_2$-macroglobulin in elderly patients with peripheral vascular disease (PVD). As $\alpha_2$-macroglobulin concentrations are a key determinant of the safety and likely to be related the tolerabilty of fibrinolytic metalloproteinases in vivo, a cross-sectional epidemiological study was conducted in patients with PVD to evaluate serum ($\alpha_2$-macroglobulin concentration and the fibrinolytic metalloproteinase binding capacity (using NAT as the test agent).

Two hundred and sixteen patients were enrolled at two centers (Cleveland Clinic Foundation, Cleveland, Ohio, and Rochester General Hospital, Rochester, N.Y.). Demographic information and other patient characteristics were collected and serum was obtained for measuring $\alpha_2$-macroglobulin, the NAT binding capacity (by titration of individual patient serum samples using an HPLC assay that detects unbound NAT) and other serum chemistry parameters. The primary endpoint was the determination of the relationship between the serum concentration of $\alpha_2$-macroglobulin and the amount of NAT (in micrograms per milliliter of serum) that could be neutralized in vitro (NAT binding capacity).

A comparison of patient characteristics in this study with those of the two largest published studies of thrombolysis in PAO (i.e., the STILE and TOPAS studies) indicated that the patient population in this study was representative of previous studies of thrombolysis in PAO; For further details on the previous studies, see Annals of Surgery, Volume 220, pages 251–266 (1994) and Ouriel et al., New England Journal of Medicine, Volume 338, pages 1105–1111 (1998), respectively.

The estimated maximum dose (EMD) for NAT was calculated for each patient using the NAT binding capacity and an estimate of each patient's plasma volume. The study results predict that the average patient could receive a dosage of 1.7 mg/kg (delivered either locally or systemically) without exceeding the capacity of $\alpha_2$-macroglobulin to bind and neutralize NAT. The results from the study are summarized in FIG. 4.

Figure 4:
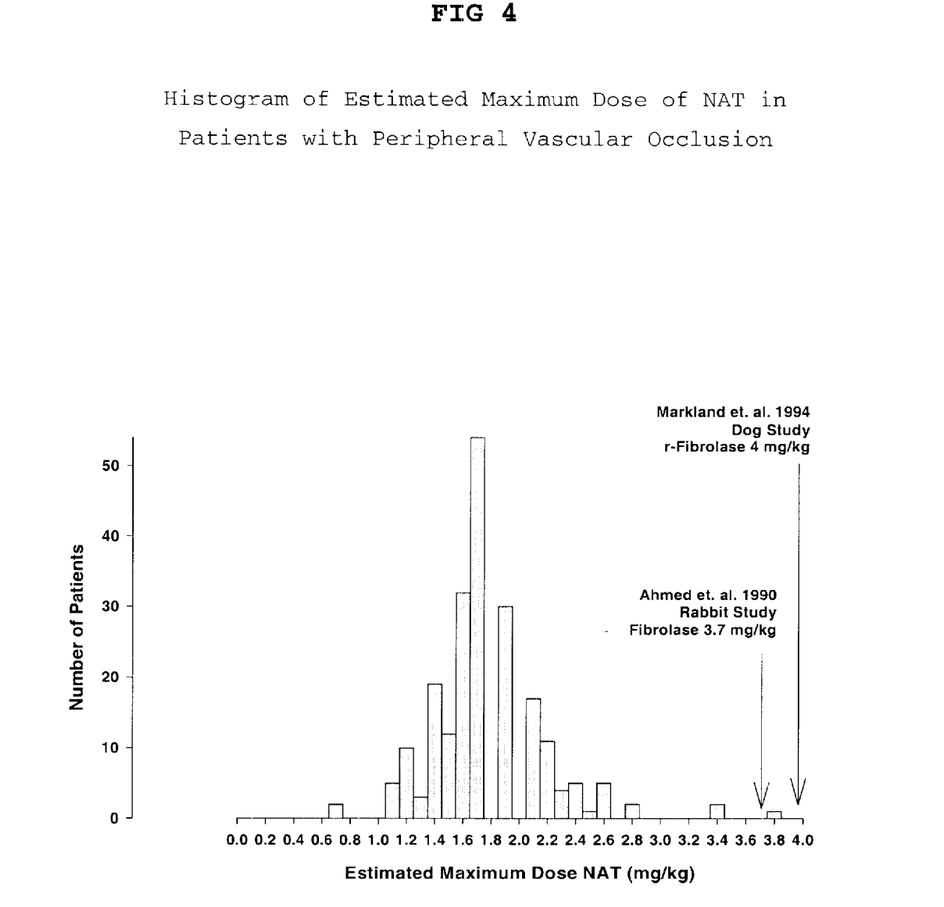
FIG. 4 is a histogram of estimated maximum dose of NAT in patients with peripheral vascular occlusion.

The estimated maximum dose of NAT was calculated for each of the 216 subjects in the study. The results for the study are depicted as a histogram, above, where a bell-shaped distribution can be observed by visual inspection. The average patient in this study is predicted to be capable of tolerating 1.7 mg/kg of NAT (the peak of the bell-shaped distribution). Dosages administered in animal studies are shown for reference (right hand side) and can be seen to be in excess of the estimated maximum dose of NAT for 99% of the study population.

Thus, the prescribed range of 0.025 to 1.7 mg/kg for the invention represents a rational estimate of the dose patients can safely receive (based on plasma volume and NAT binding capacity for ($\alpha_2$-macroglobulin) without the appearance of free NAT in the circulation.

In conclusion, the results from the exemplified pharmacology studies, Examples 1–4, above, indicate the biological effectiveness of a fibrinolytic metalloproteinase as a clot lysing agent in an animal model of thrombosis where the thrombus is comparable in size and age to that frequently encountered in peripheral arterial occlusion in humans. The dosages identified in the animal models were obtained without regard for or assessment of the potential toxicities in the animal. The effective dosages in rabbits and dogs (3.7 and 4.0 mg/kg, respectively) as described by Ahmed et al. and Markland et al. (above) might enable a veterinary use for fibrinolytic metalloproteinases. However, when considered in the presence of human data, the administration of doses of 3.7 and 4.0 mg/kg would have overdosed 99 percent of the study population. Therefore, the published animal studies do not enable the therapeutic use of fibrinolytic metalloproteinases in humans in a manner that is safe as well as biologically effective. The data presented in Example 5, on the other hand, do enable such use in humans.

What is claimed is:

1. A method for therapeutic treatment in a human subject of a blood clot, comprising locally administering to the blood clot by catheter delivery means a quantity of a fibrinolytic metalloproteinase that complexes with alpha-two macroglobulin, in an amount sufficient to facilitate lysing of the clot while not exceeding levels significantly above saturable level of alpha-two macroglobulin in said human subject, in a pharmaceutically acceptable solution, wherein the amount is in the range between 0.025 and 1.7 milligrams of the fibrinolytic metalloproteinase per kilogram of body weight of the human subject being treated.

2. The method of claim 1 in which the amount of the fibrinolytic metalloproteinase is in the range from about 0.1 to about 0.5 milligram per kilogram of body weight.

3. The method of claim 1 in which the fibrinolytic metalloproteinase is delivered via intrathrombus administration.

4. The method of claim 1 in which the fibrinolytic metalloproteinase is administered in the close proximity of the blood clot.

5. The method of claim 1 in which the blood clot is located in an artery.

6. The method of claim 5 which is used to treat peripheral artery occlusion.

7. The method of claim 1 in which the blood clot is located in a vein.

8. The method of claim 1 in which the catheter delivery means comprises a "side hole" catheter device.

9. The method of claim 1 in which the catheter delivery means comprises a "pressure response outlet" (PRO) catheter delivery device.

10. The method of claim 9 in which the solution of fibrinolytic metalloproteinase is administered by pulse-spray infusion.

11. The method of claim 10 in which a pulse volume of from about 0.1 to about 0.5 milliliter of fibrinolytic metalloproteinase solution is administered.

12. The method of claim 1 in which the fibrinolytic metalloproteinase is present at a concentration in the range from about 0.1 to about 80 milligrams per milliliter.

13. The method of claim 1 in which the fibrinolytic metallaproteinase is Novel Acting Thrombolytic (NAT).

14. The method of claim 1 in which the fibrinolytic metalloproteinase is fibrolase.

* * * * *